US012766053B2

(12) United States Patent
Gomes et al.

(10) Patent No.: US 12,766,053 B2
(45) Date of Patent: Oct. 20, 2026

(54) TRANSPORTABLE COMPUTED TOMOGRAPHY (CT) SCANNING SYSTEM

(71) Applicant: Heart of Australia Pty Ltd, Chelmer QLD (AU)

(72) Inventors: Kylie Anne Gomes, Kenmore Hills QLD (AU); Rolf Gomes, Kenmore Hills QLD (AU)

(73) Assignee: Heart of Australia Pty Ltd, Chelmer (AU)

( * ) Notice: Subject to any disclaimer, the term of this patent is extended or adjusted under 35 U.S.C. 154(b) by 188 days.

(21) Appl. No.: 18/686,204

(22) PCT Filed: Aug. 25, 2022

(86) PCT No.: PCT/AU2022/050996

§ 371 (c)(1),
(2) Date: Feb. 23, 2024

(87) PCT Pub. No.: WO2023/023769

PCT Pub. Date: Mar. 2, 2023

(65) Prior Publication Data

US 2025/0186275 A1 Jun. 12, 2025

(30) Foreign Application Priority Data

Aug. 25, 2021 (AU) ................................ 2021902718

(51) Int. Cl.

*A61G 3/00* (2006.01)
*A61B 6/00* (2024.01)

(Continued)

(52) U.S. Cl.

CPC .............. *A61G 3/001* (2013.01); *A61B 6/032* (2013.01); *A61B 6/4405* (2013.01); *A61B 6/56* (2013.01);

(Continued)

(58) Field of Classification Search

CPC ...... A61G 3/001; A61B 6/032; A61B 6/4405; A61B 6/56; H02J 9/06

See application file for complete search history.

(56) References Cited

U.S. PATENT DOCUMENTS 5,808,376 A 9/1998 Gordon et al.
2007/0202836 A1 * 8/2007 Zaman .................. G06F 1/3203 455/343.2

(Continued)

FOREIGN PATENT DOCUMENTS

AU 2021107157 A4 12/2021
CN 112667009 A * 4/2021

(Continued)

OTHER PUBLICATIONS

International Search Report and Written Opinion issued in International Application No. PCT/AU2022/050996, dated Oct. 4, 2022 (9 pages).

(Continued)

*Primary Examiner* — Uzma Alam
*Assistant Examiner* — Richard O Toohey
(74) *Attorney, Agent, or Firm* — Rothwell, Figg, Ernst & Manbeck, P.C.

(57) ABSTRACT

A transportable computed tomography (CT) scanning system including a transportable structure, a computed tomography (CT) scanner located on the transportable structure, and an onboard power supply system connected to the CT scanner and located on the transportable structure.

16 Claims, 5 Drawing Sheets

(51) Int. Cl.
*A61B 6/03* (2006.01)
*H02J 7/35* (2006.01)
*H02J 7/50* (2026.01)
*H02J 9/06* (2006.01)

(52) U.S. Cl.
CPC .................. *H02J 7/50* (2026.01); *H02J 9/06* (2013.01); *A61G 2210/50* (2013.01); *H02J 7/35* (2013.01)

(56) References Cited

U.S. PATENT DOCUMENTS

| | | | | |
|---|---|---|---|---|
| 2016/0242705 | A1* | 8/2016 | Richardson .............. | A61B 6/56 |
| 2018/0263591 | A1* | 9/2018 | Shanthakumar ........ | H02J 9/062 |
| 2022/0151844 | A1 | 5/2022 | Shizukushi | |

FOREIGN PATENT DOCUMENTS

| | | | | |
|---|---|---|---|---|
| JP | 2015107161 | A | * | 6/2015 |
| WO | WO 2021006294 | A1 | * | 1/2021 |

OTHER PUBLICATIONS

International Preliminary Report on Patentability issued in International Application No. PCT/AU2022/050996, dated Sep. 14, 2023 (6 pages).

* cited by examiner

TRANSPORTABLE COMPUTED TOMOGRAPHY (CT) SCANNING SYSTEM

CROSS REFERENCE TO RELATED APPLICATION

This application is a 35 U.S.C. § 371 National Phase Entry Application from PCT/AU2022/050996, filed Aug. 25, 2022, designating the United States, which claims priority to Australian Patent Application No. 2021902718, filed Aug. 25, 2021, the disclosures of which are incorporated herein by reference in their entirety.

TECHNICAL FIELD

The present invention relates to a transportable computed tomography (CT) scanning system. In some preferable embodiments, the invention relates to a power supply system for a transportable CT scanning system.

BACKGROUND

Any references to methods, apparatus or documents of the prior art are not to be taken as constituting any evidence or admission that they formed, or form part of the common general knowledge.

Computed tomography (CT) is a well and widely known and used medical imaging process capable of creating a 3D image of the inside of an object.

CT scanners and imaging systems require complex setups to ensure that the scanner has sufficient power but also to ensure that the operation of the scanner is safe, by way of shielding and cooling, for example. In particular, CT scanners require large quantities of electrical power in short bursts which can be difficult to source in remote and regional areas.

As a result of these complex setups, it is incredibly difficult to transport CT scanners, meaning that those seeking to have a scan performed must travel to the dedicated CT scanning location. This creates significant barriers for those in regional areas whose hospitals and health services may be underserviced and do not have access to CT scanners.

SUMMARY OF INVENTION

In an aspect, the invention provides a transportable computed tomography (CT) scanning system comprising:

a transportable structure;

a computed tomography (CT) scanner located on the transportable structure; and an onboard power supply system connected to the CT scanner and located on the transportable structure.

Preferably, the transportable structure comprises wheels. Preferably, the transportable structure comprises one or more trailers having wheels.

Preferably, the power supply system comprises:

an uninterruptable power supply (UPS) connected to the CT scanner and configured to deliver power to operate the CT scanner;

one or more batteries connected to the UPS.

Preferably, the power supply system further comprises an isolation transformer connected to a main switchboard and the CT scanner. Preferably, the main switchboard is connected to the UPS. Preferably, the power supply system further comprises one or more general power outlets (GPOs) configured to receive electricity to recharge the one or more batteries.

Preferably, the one or more batteries are rechargeable batteries.

Preferably, the power supply system further comprises a solar power system connected to the one or more batteries.

Preferably, the transportable computed tomography (CT) scanning system further comprises an x-ray scanner located on the transportable structure. Preferably, the x-ray scanner is connected to the onboard power supply system.

Preferably, the onboard power supply system further comprises a generator.

In another aspect, the invention provides a transportable computed tomography (CT) scanning system comprising:

a transportable structure comprising one or more trailers;

a computed tomography (CT) scanner located on the transportable structure; and an onboard power supply system connected to the CT scanner and located on the transportable structure, the onboard power supply system comprising an uninterruptable power supply (UPS) connected to the CT scanner and configured to deliver power to operate the CT scanner, one or more batteries connected to the UPS, and at least one general power outlet (GPO) located on one of the one or more trailers and configured to receive electricity to recharge the one or more batteries.

Preferably, the onboard power supply system is configured to supply sufficient power to the CT scanner via the UPS and one or more batteries. More preferably, the onboard power supply system is configured to only supply power to the CT scanner via the UPS and one or more batteries. Even more preferably, the onboard power supply system is configured to only supply power to the CT scanner via the UPS and one or more batteries when one or more generators are not in use or in operation.

Preferably, the onboard power supply system is configured to operate in a discharge cycle and recharge cycle. Preferably, in the discharge cycle, the UPS provides power to the CT scanner. Preferably, the one or more generators are not operational during the discharge cycle. Preferably, in the recharge cycle, the one or more generators recharge the one or more batteries of the UPS. Preferably, the UPS is not providing power to the CT scanner during the recharge cycle. Preferably, only one of the recharge cycle and the discharge cycle may be performed at a time. Preferably, the recharge cycle and the discharge cycle cannot be performed simultaneously.

In another aspect, the invention provides a method of operating a transportable computed tomography (CT) scanning system including the steps of:

operating a computed tomography (CT) scanner located on a transportable structure, wherein the CT scanner draws sufficient power from an uninterruptable power supply (UPS) having one or more batteries.

Preferably, the CT scanner is located on a transportable structure. Preferably, the transportable structure takes the form of a semi-trailer.

Preferably, the method further includes the step of recharging the one or more batteries via a generator while the CT scanner is not in operation.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

FIGS. 1 to 4 illustrate a transportable computed tomography (CT) scanning system 10 including a transportable structure (in the form of a first semi-trailer 100) and a computed tomography (CT) scanner 102 located on the transportable structure. The transportable CT scanning system 10 also includes an onboard power supply system (illustrated in FIG. 5) connected to the CT scanner 102 and located on the transportable structure.

The onboard power supply system includes an uninterruptable power supply (UPS) 104 connected to the CT scanner 102 which is configured to deliver power to operate the CT scanner 102, and a plurality of rechargeable batteries 106 connected to the UPS 104 for storing power to be delivered to the CT scanner 102 via the UPS 104. This is advantageous because the CT scanner 102 can operate even when grid or mains power is not directly or consistently available.

Figure 6:
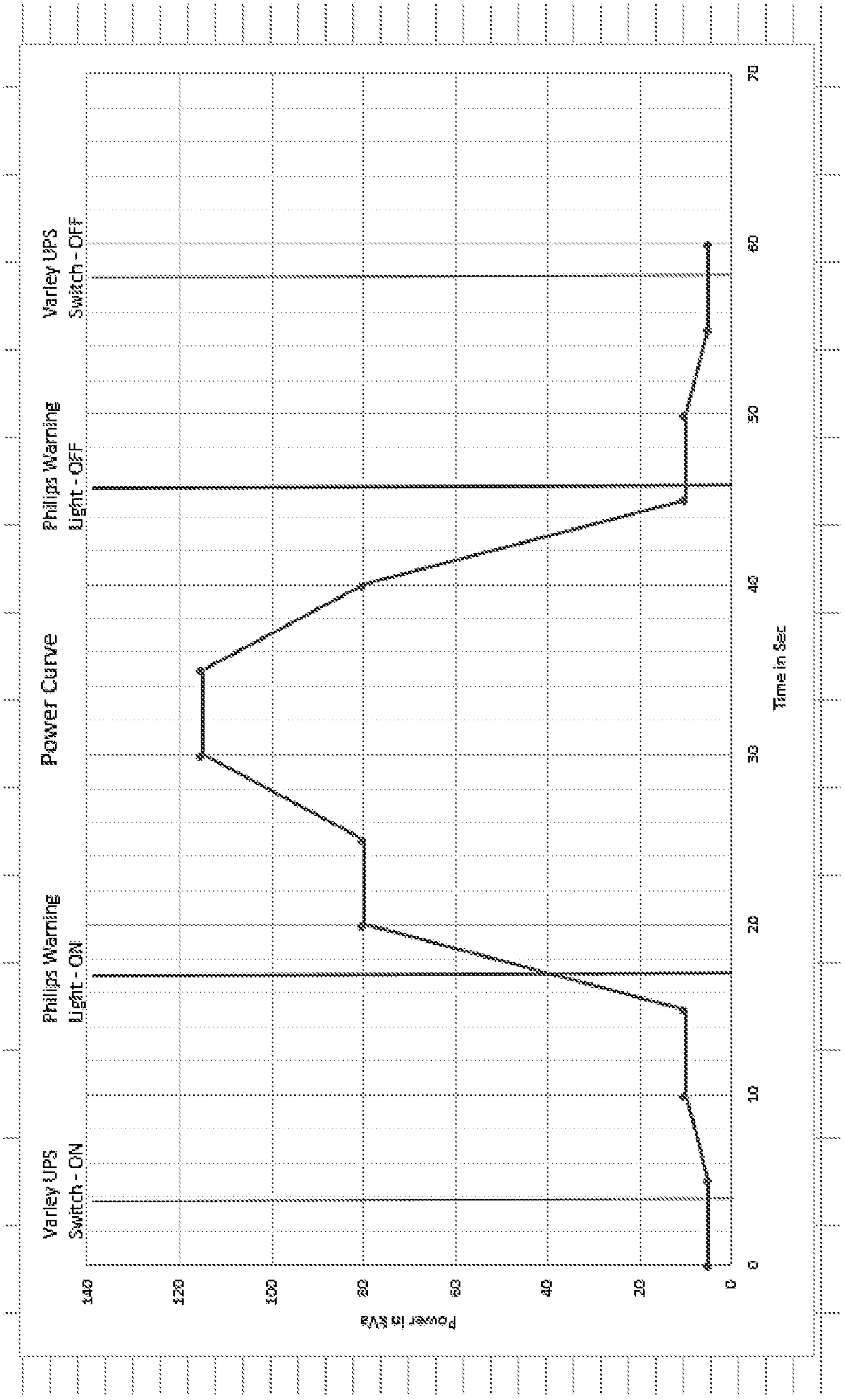
FIG. 6 is an illustration of a draw profile of the transportable CT scanning system.

The UPS 104 is configured to deliver sufficient power for the CT scanner 102 to operate and perform at least one scan before the batteries 106 need to be recharged. With reference to FIG. 6, the load and draw profile of a CT scanner 102 over time can be seen. It will be appreciated that the CT scanner 102 requires a high amount of power (approximately 120 kVa) in order to operate but this large amount of power is only required for a reasonably short amount of time (approximately 8 seconds at full power).

As can be seen in the figures, the transportable structure comprises two vehicle trailers in the form of the first semi-trailer 100 and a second semi-trailer 108, each having a number of wheels 101 and the CT scanner 102 is located within the first semi-trailer 100 for transporting.

Figure 5:
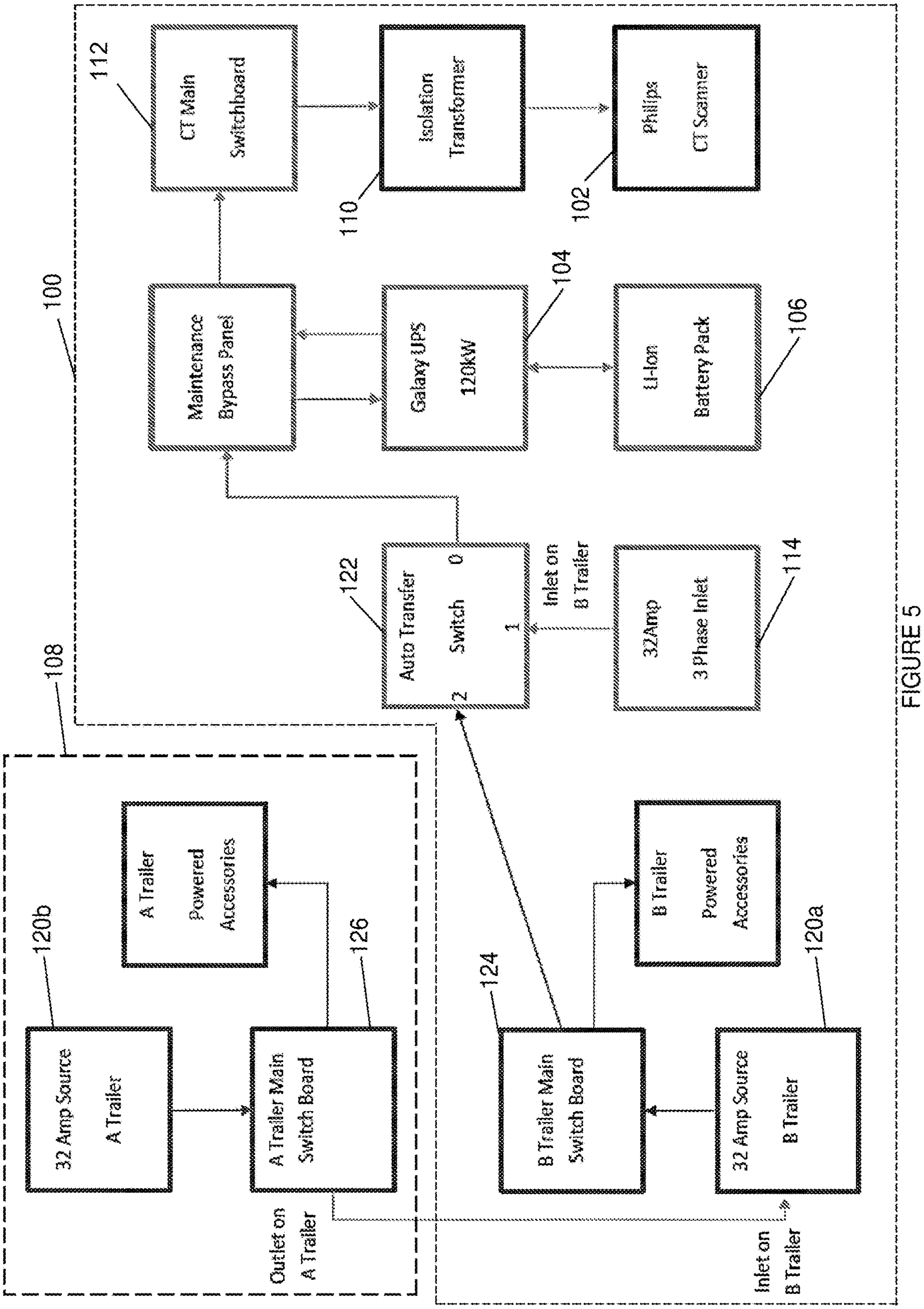
FIG. 5 is an block diagram of the power distribution system of the transportable CT scanning system.

The configuration of the onboard power supply system can be seen in greater detail in FIG. 5, and is shown to include an isolation transformer 110 connected to a main switchboard 112 and the CT scanner 102, wherein the main switchboard 112 is connected to the UPS 104. In addition, the onboard power supply system further includes at least one general power outlet (GPO) 114 configured to receive electricity to recharge the one or more batteries 106. The GPO is, preferably, a 3-phase, 32 Amp rated inlet located on the first semi-trailer 100 and is connected to the UPS 104 and CT scanner 102 to provide power to the batteries 106. In some embodiments, the GPO 114 can provide power directly to the CT scanner 102.

Figure 1:
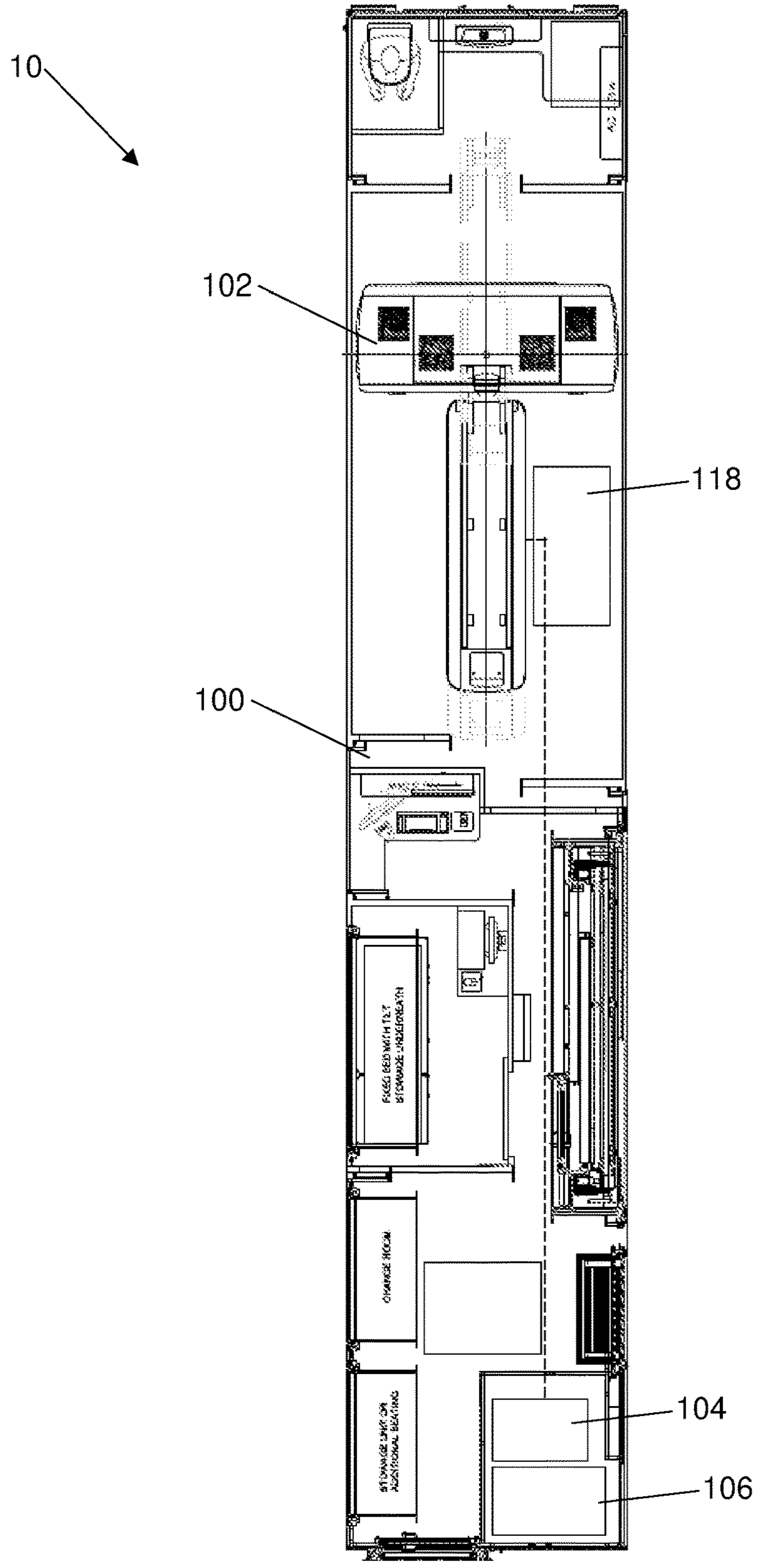
FIG. 1 is an overhead, interior view of a transportable CT scanning system according to an embodiment of the present invention.
Figure 2:
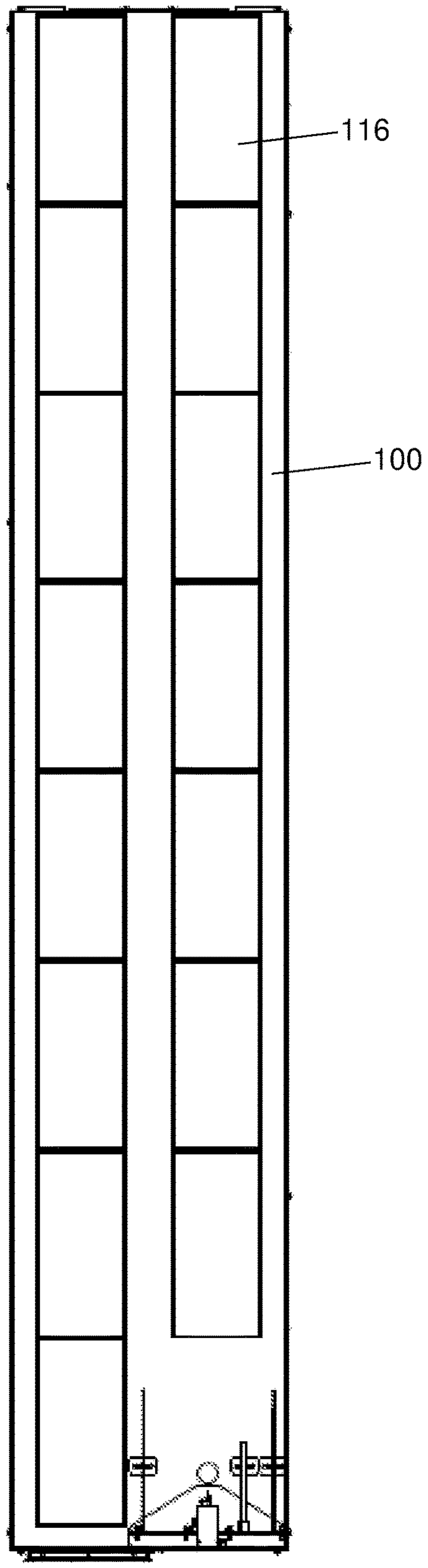
FIG. 2 is an overhead, exterior view of the transportable CT scanning system of FIG. 1.
Figure 3:
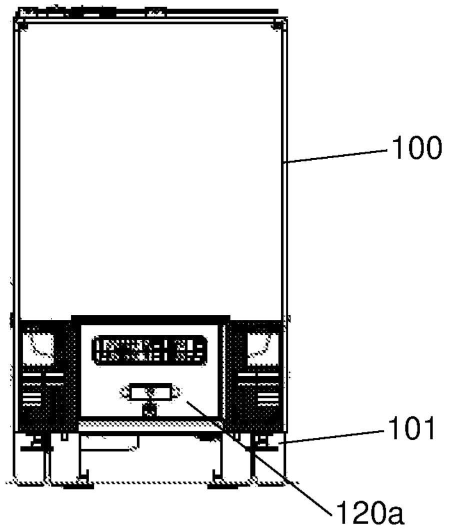
FIG. 3 is a rear view of the transportable CT scanning system of FIG. 1.
Figure 4:
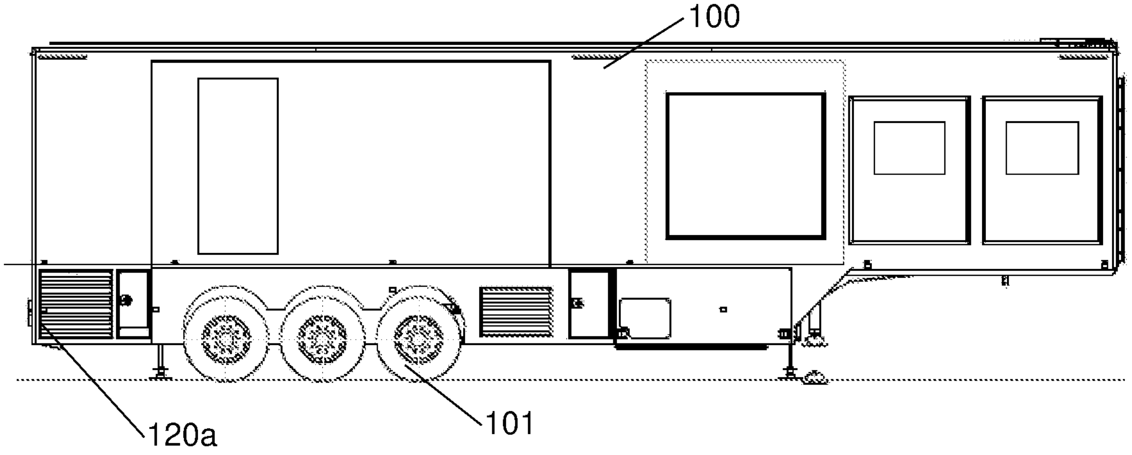
FIG. 4 is a side view of the transportable CT scanning system of FIG. 1.

In some embodiments, as shown in FIG. 2, the power supply system also includes a solar power system 116 which can be connected to the one or more batteries 106 to recharge the batteries 106. This provides an auxiliary or supplementary recharge system for the rechargeable batteries 106, in addition to, or in the absence of, power supplied from the GPO 114 and/or the generators (described below).

The illustrated embodiment also includes an optional x-ray scanner 118 located on the transportable structure. The x-ray scanner 118 is connected to and powered by the onboard power supply system.

The onboard power supply system also includes a generator 120*a*, 120*b* located on each of the first semi-trailer 100 and the second semi-trailer 108 for providing power to the UPS 104 to power the CT scanner 102. The generators 120*a*, 120*b* are located remotely from the CT scanner 102 (relative to the location of the CT scanner 102 within the first semi-trailer 100) to minimise disruption and damage to the sensitive scanning equipment that can be caused by the excessive vibrations and heat generated by the generators 120*a*, 120*b*.

In the first semi-trailer 100, shown in FIGS. 1-4, the generator 120*a* located thereon is located at the rear of the first semi-trailer 100 which is relatively remote from the CT scanner 102.

The second generator 120*b*, located in the second semi-trailer 108, is able to be connected to the first semi-trailer 100 via switchboards 124, 126 as illustrated in FIG. 5, thereby completely isolating the first semi-trailer 100 and the CT scanner 102 onboard from the vibrations and heat of the second generator 120*b* while still providing power to the CT scanner 102 and/or the rechargeable batteries 106.

Ideally, the first and second generators 120*a*, 120*b* are only in operation when the CT scanner 102 is not and thus the first and second generators 120*a*, 120*b* can be used to recharge the batteries 106 after they have been dissipated to mitigate any adverse effects from the operation of the generators 120*a*, 120*b* while the CT scanner 102 is in use. This effectively isolates the generators 120*a*, 120*b* from the CT scanner 102.

In use, the onboard power supply system is configured to operate in a discharge cycle and recharge cycle. In the discharge cycle, the UPS 102 provides power to the CT scanner 102 and the generators 120*a*, 120*b* are not operational during the discharge cycle. Subsequently, in the recharge cycle, the generators 120*a*, 120*b* recharge the batteries 106 of the UPS 104 and the UPS 104 is not providing power to the CT scanner 102 during the recharge cycle. The onboard power supply system is preferably configured such that the recharge cycle and the discharge cycle cannot be performed simultaneously.

The batteries 106 of the UPS 104 can also be recharged through the GPO 114. To minimise use of the generators 120*a*, 120*b*, an Auto Transfer Switch (ATS) 122 is utilised so that when mains power is available through the GPO 114, the system will prioritise drawing energy from a mains power source. However, in the absence of a mains power source, or the loss of power, the ATS 122 will switch to drawing electrical power from the generators 120*a*, 120*b* to ensure the batteries 106 are recharged.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step, etc.

The above detailed description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

Throughout the specification and claims (if present), unless the context requires otherwise, the term "substantially" or "about" will be understood to not be limited to the specific value or range qualified by the terms.

The invention claimed is:

1. A transportable computed tomography (CT) scanning system comprising:
- a transportable structure;
- a computed tomography (CT) scanner located on the transportable structure; and
- an onboard power supply system connected to the CT scanner and located on the transportable structure, wherein the power supply system comprises:
- an uninterruptable power supply (UPS) connected to the CT scanner and configured to deliver power to operate the CT scanner;
- one or more batteries connected to the UPS,
- wherein the onboard power supply system further comprises an isolation transformer connected to a main switchboard and the CT scanner;
- wherein the main switchboard is connected to the UPS;
- wherein the onboard power supply system is configured to only supply power to the CT scanner via the UPS and one or more batteries when one or more generators are not in use or in operation,
- wherein the onboard power supply system is configured to operate in a discharge cycle and recharge cycle,
- wherein in the discharge cycle, the UPS provides power to the CT scanner,
- wherein the one or more generators are not operational during the discharge cycle,
- wherein in the recharge cycle, the one or more generators recharge the one or more batteries of the UPS and,
- wherein the UPS is not providing power to the CT scanner during the recharge cycle, and
- wherein the UPS is a primary source of power supply for operating the CT scanner.

2. The transportable CT scanning system of claim 1, wherein the power supply system further comprises one or more general power outlets (GPOs) configured to receive electricity to recharge the one or more batteries.

3. The transportable CT scanning system of claim 1, wherein the power supply system further comprises a solar power system connected to the one or more batteries.

4. The transportable CT scanning system of claim 1, wherein the transportable computed tomography (CT) scanning system further comprises an x-ray scanner located on the transportable structure.

5. The transportable CT scanning system of claim 4, wherein the x-ray scanner is connected to the onboard power supply system.

6. The transportable CT scanning system of claim 4, wherein the onboard power supply system is configured to supply sufficient power to the CT scanner via the UPS and one or more batteries.

7. The transportable CT scanning system of claim 1, wherein the transportable structure comprises wheels.

8. The transportable CT scanning system of claim 1, wherein the one or more generators are positioned away from the CT scanner such that disruption and damage to the CT scanner from vibrations and heat emitted by the one or more generators is minimized.

9. The transportable CT scanning system of claim 1, wherein the one or more generators are positioned away from the CT scanner such that the CT scanner is neither disrupted nor damaged from vibrations and heat emitted by the one or more generators.

10. A transportable computed tomography (CT) scanning system comprising:
- a transportable structure comprising one or more trailers;
- a computed tomography (CT) scanner located on the transportable structure; and
- an onboard power supply system connected to the CT scanner and located on the transportable structure, the onboard power supply system comprising an uninterruptable power supply (UPS) connected to the CT scanner and configured to deliver power to operate the CT scanner, one or more batteries connected to the UPS, and at least one general power outlet (GPO) is located on one of the one or more trailers and configured to receive electricity to recharge the one or more batteries,
- wherein the onboard power supply system is configured to only supply power to the CT scanner via the UPS and one or more batteries when one or more generators are not in use or in operation,
- wherein the onboard power supply system is configured to operate in a discharge cycle and recharge cycle,
- wherein in the discharge cycle, the UPS provides power to the CT scanner,
- wherein the one or more generators are not operational during the discharge cycle,
- wherein in the recharge cycle, the one or more generators recharge the one or more batteries of the UPS and,
- wherein the UPS is not providing power to the CT scanner during the recharge cycle, and
- wherein the UPS is a primary source of power supply for operating the CT scanner.

11. The transportable CT scanning system of claim 10, wherein the onboard power supply system is configured to supply sufficient power to the CT scanner via the UPS and one or more batteries.

12. The transportable CT scanning system of claim 10, wherein the one or more generators are positioned away from the CT scanner such that disruption and damage to the CT scanner from vibrations and heat emitted by the one or more generators is minimized.

13. The transportable CT scanning system of claim 10, wherein the one or more generators are positioned away from the CT scanner such that the CT scanner is neither disrupted nor damaged from vibrations and heat emitted by the one or more generators.

14. A method of operating a transportable computed tomography (CT) scanning system including the steps of:

operating a computed tomography (CT) scanner located on a transportable structure;

wherein the CT scanner draws sufficient power from a power supply system;

wherein the power supply system comprises an uninterruptable power supply (UPS) connected to the CT scanner, the UPS having one or more batteries, wherein the power supply system further comprises an isolation transformer connected to a main switchboard and the CT scanner;

wherein the main switchboard is connected to the UPS;

wherein the power supply system is configured to only supply power to the CT scanner via the UPS and one or more batteries when one or more generators are not in use or in operation, wherein the power supply system is configured to operate in a discharge cycle and recharge cycle, wherein in the discharge cycle, the UPS provides power to the CT scanner, wherein the one or more generators are not operational during the discharge cycle, wherein in the recharge cycle, the one or more generators recharge the one or more batteries of the UPS and, wherein the UPS is not providing power to the CT scanner during the recharge cycle, and wherein the UPS is a primary source of power supply for operating the CT scanner.

15. The method of claim 14, wherein the one or more generators are positioned away from the CT scanner such that disruption and damage to the CT scanner from vibrations and heat emitted by the one or more generators is minimized.

16. The method of claim 14, wherein the one or more generators are positioned away from the CT scanner such that the CT scanner is neither disrupted nor damaged from vibrations and heat emitted by the one or more generators.

* * * * *